United States Patent [19]

Barany

[11] Patent Number: 4,719,179
[45] Date of Patent: Jan. 12, 1988

[54] SIX BASE OLIGONUCLEOTIDE LINKERS AND METHODS FOR THEIR USE

[75] Inventor: Francis Barany, Baltimore, Md.

[73] Assignee: Pharmacia P-L Biochemicals, Inc., Milwaukee, Wis.

[21] Appl. No.: 676,935

[22] Filed: Nov. 30, 1984

[51] Int. Cl.$^4$ .................. C12N 15/00; C12P 19/34; C07H 15/12

[52] U.S. Cl. .................. 435/172.1; 435/172.3; 435/91; 536/27; 935/10

[58] Field of Search .................. 435/172.3; 935/6, 10; 536/27

[56] References Cited

PUBLICATIONS

G. R. Gough et al., 23 *Tetrahedron Letters*, 3439-3442 (1982).
J. Stawinski et al., 4 *Nucleic Acids Research*, 353-371 (1977).
R. Rothstein et al., 68 *Meth. Enzym.*, 98-109 (1979).
R. Lathe et al., 20 *Gene*, 187-195 (1982).
J. Boeke, 181 *Mol. Gen. Genet*, 288-291 (1981).
J. Stone et al., 37 *Cell*, 549-558 (1984).
J. Vieira et al., 19 *Gene*, 259-268 (1982).
F. Heffron et al., 75 *Proc. Natl. Acad. Sci.*, USA, 6012-6016 (1978).
C. Bahl et al., 1 *Gene*, 81-92 (1976).
C. Bahl et al., 81 *Biochem. & Biophys.*, 685-703 (1978).
A. Maxam et al., 65 *Meth. Enzym.*, 499-560 (1977).
A. Banaszuk et al., 128 *Anal. Biochem.*, 281-286 (1983).
D. Hanahan, 166 *J. Mol. Biol.*, 577-580 (1983).
D. Holmes et al., 114 *Anal. Biochem.*, 193-197 (1981).
G. Gough et al., 7 *Nucleic Acids Research*, 1955-1964 (1979).
A. Sood et al., 4 *Nucleic Acids Research*, 2757-2765 (1977).
C. Reese et al., 30 *Tetrahedron Letters*, 2727-2730 (1978).
J. Stawinski et al., 54 *Can. J. Chem.*, 670 (1976).
Barany, F., *Gene*, 37:111-123, 1985.
Barany, F., *P.N.A.S.(USA)*, 82:4202-4206, 1985 (Jun.).
Roberts, R., *Nucl. Ac. Research*, 13:r165-r207, 1985.
Barton et al, *P.N.A.S.(USA)*, 82:6460-6464, 1985 (Oct.).
Hertzberg et al., *J. Am. Chem. Soc.*, 104:313-315, 1982.

*Primary Examiner*—Thomas G. Wiseman
*Assistant Examiner*—Thomas D. Mays
*Attorney, Agent, or Firm*—Quarles & Brady

[57] ABSTRACT

A method for inserting a selected restriction site into a double stranded genetic sequence at a selected tab site, and a linker for use therewith are disclosed. The method involves treating the genetic sequence with an opening agent (such as a restriction enzyme) so as to open both strands of the tab site. One then exposes the opened genetic sequence to two hexameric single stranded oligonucleotide linkers in the presence of a ligating enzyme. The two linkers have the same nitrogenous base sequence, a sequence which is partially palindromic complementary to itself at least one end of the nitrogenous sequence, but is not completely palindromic complementary to itself. Through use of this method, the two linkers are inserted in the opening with partial complementary overlap, and at least one of the linkers is affixed to each strand. Subsequently, the site is reclosed at the point of the insertion so as to contain a six base insertion.

6 Claims, No Drawings

SIX BASE OLIGONUCLEOTIDE LINKERS AND METHODS FOR THEIR USE

BACKGROUND OF THE INVENTION

A. Field Of The Invention

This invention relates to recombinant-DNA technology. More specifically, it relates to linkers which can be used to insert specified restriction sites into a gene sequence, and to methods which permit the use of these linkers.

B. Description Of The Art

The inventor expresses his gratitude to The Helen Hay Whitney Foundation for its financial support, and to Johns Hopkins University for the use of their laboratories in connection with this invention.

Enzymatic cleavage and joining of DNA is of central importance to the generation of recombinant-DNA molecules. However, a limiting factor in many cloning strategies was that researchers had to rely on only those restriction sites provided by nature. This was a problem because in some cases appropriate restriction sites were not present at the right locations. Moreover, in other cases the desired restriction site was present at too many points in the gene sequence, and thus could not be selectively used.

In order to understand an approach that the prior art chose to try to solve these problems, it is important to have an understanding of the terms "nucleotide" and "oligonucleotide". "Nucleotides" are organic compounds having a nitrogenous base, a five carbon backbone (usually a sugar) and a phosphoric acid group. Many nitrogenous bases are derived from purine and pyrimidine such as uracil ("U"), thymine ("T"), cytosine ("C"), 5-methyl cytosine, 5-hydroxymethyl cytosine, adenine ("A"), guanine ("G"), 2-methyladenine, 1-methylguanine. "Nucleosides" are usually N-glycosides of these pyrimidine or purine bases. Among these are the ribonucleosides which contain D-ribose as the sugar component, and the 2' deoxyribonucleosides which contain 2'-deoxy-D-ribose as the sugar component. The most prevalent nucleosides are adenosine, guanosine, cytidine, uridine, 2' deoxyadenosine, 2' deoxyguanosine, 2' deoxycytidine, and 2' deoxythymidine.

The names for the corresponding "nucleotides" are the same except that "5'-phosphoric acid" is added to reflect the presence of a phosphate group. The nucleotides are also known by their abbreviations AMP, GMP, CMP, UMP, dAMP, dGMP, dCMP, and dTMP. These nucleotides can also occur as the 5' di-phosphates and the 5' triphosphates (e.g. ADP, ATP). As used herein, the term "nucleotide" is meant to refer to all of these variants, as well as similar variants such as where the nitrogenous base or the sugar backbone is further modified.

"Oligonucleotides" are compounds made by linking a relatively small number (e.g. less than twenty) nucleotides together in a sequence. The term is also meant to include compounds where the 5' end of the oligonucleotide is OH rather than phosphate, and other similar variants. The sequence of an oligonucleotide is normally labeled by reference to the sequence of its nitrogenous bases. The five most prevalent bases are those that have been abbreviated above by the letters A, G, T, C, and U.

To solve the problems described above, the art developed eight and ten base *double* stranded oligonucleotides (also known as "adaptors") that had a base sequence recognized by the desired restriction enzyme. See e.g. F. Heffron et al, 75 P.N.A.S. USA 6012–6016 (1978). (The disclosure of this reference and all other articles cited herein are incorporated by references as if fully set forth below.) These Heffron et al. adaptors were ligated into blunt ends randomly produced by DNAase I, thereby converting these sites to the desired specificity.

In writing out the sequence of a double stranded eight base oligonucleotide adaptor, it was conventional to abbreviate the oligonucleotide by writing a first strand 5' to 3' such as 5'-CCCCGGGG-3', and then writing underneath it in the reverse direction (3' to 5') the complementary strand. For example:

5'-CCCCGGGG-3'

3'-GGGGCCCC-5'

In this regard, G is known to be complementary to C, T is known to be complementary to A, and A is known to be complementary to U.

One problem with the above described approach is that amino acids are coded for in three base groupings (e.g. CCC-CGG-GG-). Thus, an eight or ten sequence adaptor has extra bases. As a result, if one inserts such an adaptor into a gene sequence, the insertion will be likely to cause frame shifts and distortions.

The art therefore developed six base ("hexameric") *double* stranded adaptors which did not have these problems. However, in view of the very short length of these adaptors, these prior art adaptors were designed so as to be completely complementary to themselves (e.g.

CCCGGG).
GGGCCC

Because of this, they were not useful for very important restriction sites which did not present "blunt" ends after cleavage (unless one was willing to first alter the restriction site ends). Moreover, if not inserted at exactly the right place in the sequence, these adaptors could cause the protein on one or both sides of the restriction site to lose or change a coded amino acid, with resulting distortions.

Other problems in the art included that once a double stranded adaptor had been formed, the adaptor would be suitable only for a site of one structure. Thus, one had to inventory many types of adaptors in the laboratory. Further, in order to cause prior art adaptors to ligate effectively, one often had to use a large excess of the adaptor. Then, one either had to purify away the excess, or waste costly restriction enzyme on eating up the excess.

The state of the prior art can be appreciated with reference to three recent articles. In one, J. D. Boeke, 181 Mol. Gen. Genet. 288–291 (1981) a two codon (six base) insertion was achieved by first cutting with an enzyme to leave two base overhanging "sticky" ends, then filling in both strands with a polymerase to gain two bases, then adding a very large adaptor having a four base segment of interest at one end, and then chopping off everything but the four bases. This method is more expensive and less efficient than the present invention, and its application is limited to very specific sequences.

The second article is J. Stone et al., 37 Cell 549-558 (1984) (not prior art) where a convoluted and inefficient process for inserting two codons was reported. Multiple twelve base adaptors were inserted into blunt end sites. Most of the excess DNA adaptor was then cut away and the DNA religated. Analysis of clones indicated multiple adaptor insertion. These clones had to be reopened and trimmed (yet again) to leave a single insertion (6 bases), and then recircularized. This method is also apparently limited to blunt end sites.

In the third article, J. Vieira et al., 19 Gene 259-268 (1982) a method is provided for inserting a restriction site of twelve bases. As before, the method is not general, and is limited to making a four amino acid insertion.

Thus, it can be seen that a need has existed for an improved means of converting restriction sites to a selected restriction enzyme specificity while creating only a six base insertion.

SUMMARY OF THE INVENTION

The present invention relates generally to single stranded linkers and methods for using them. In one embodiment, there is provided a method for inserting a selected restriction site into a double stranded genetic sequence at a selected "tab" site. The method comprises treating the genetic sequence with an opening agent so as to open both strands of the selected tab site. Thereafter, one exposes the opened genetic sequence to two hexameric single stranded oligonucleotide linkers in the presence of a ligating enzyme. The two linkers have the same nitrogenous base sequence, a sequence which is partially "palindromic complementary" to itself at an end of the sequence, but is not completely "palindromic complementary" to itself. The two linkers are inserted in the opening with partial complementary overlap, with at least one linker being affixed to each strand. Preferably, the genetic sequence is a DNA sequence on a recombinant vector (e.g. a plasmid).

A "tab" site is a standard restriction enzyme site, a site openable by a restriction enzyme under non-standard conditions, a site openable by chemical agents, or a site otherwise openable by an "opening agent" to provide non-blunt ends. The "opening agent" is usually a restriction enzyme, but might also be a chemical or other opener.

In a second aspect of the invention, there is provided a hexameric single stranded oligonucleotide linker having a nitrogenous base sequence which is partially palindromic complementary at an end of the base sequence, but not completely palindromic complementary.

In understanding the present invention, it is useful to note that a sequence such as CCCGGG is a "blunt end" sequence which is completely "palindromic complementary" (i.e. when the sequence is reversed it matches with no overlap):

5'-CCCGGG-3'

3'-GGGCCC-5'

However, a sequence in accordance with the present invention, such as AGCTCG, is *partially*, but not completely palindromic complementary (i.e. the reversed sequence matches up only partially at at least one end):

```
    AGCTCG    or    AGCTCG
GCTCGA              GCTCGA
```

Note that this particular linker can match up in *two* ways, one to provide a two-base 3' overhang, and the other to provide a 4-base 5' overhang. Alternatively, other such linkers will line up to provide a two-base 5' overhang and also a 4-base 3' overhang. Thus, linkers of this type can make sticky end ligations from both sides.

Other partially palindromic complementary sequences can be generated from the formulas which follow. In these formulas (and in the claims that use them), B, D, E, and F are any nucleotides, and B', D', E', and F' are their respective complements. For example, DEF'-D'E'F might be inter alia AATTTA or GCACGT.

The most important four formulas are:

| Type | General Formula Pre-existing Site | General Formula For Linker | Example of Pre-existing Site | Linker Example |
|---|---|---|---|---|
| Four base-5' overhang | 5'-B D E E'D' B'-3'<br>3'-B' D'E'E D B -5' | DEE'D'FF' | A_____AGCTT<br>TTCGA_____A | AGCTGC |
| Two base-5' overhang | 5'-B D D' B'-3'<br>3'-B' D'D B -5' | DD'EFF'E' | C_____CGG<br>GGC_____C | CGAATT |
| Two base-3' overhang | 5'-B D D' B'-3'<br>3'-B' D'D B -5' | EFF'E'DD' | GCG_____C<br>C_____GCG | AGCTCG |
| Four base-3' overhang | 5'-F E B B'E' F'-3'<br>3'-F' E'B'B E F -5' | D'DEBB'E' | GGGCC_____C<br>C_____CCGGG | GCGGCC |

Still other linkers are meant to be within the scope of the present invention, provided that the feature of partial "palindromic complementariness" is maintained. Note that a sequence such as AAATTC is *not* "partially palindromic complementary" as that term is used herein even though the middle region AATT is complementary to itself (because neither end is complementary).

Another aspect of the present invention is that notwithstanding the very short length of the six base linker, and the even shorter section of overlap between the two single stranded linkers when they are inserted, the linker is able to readily bind to the staggered ends of the restriction site and to the complementary linker. Yet, in solution the linkers remain single stranded and therefore do not create restriction sites until they actually link up with the opened DNA.

This permits the subsequent steps of the reaction to be run without purifying away the excess linker (which excess was needed to cause the ligation reaction to occur). With double stranded adaptors, purification to remove excess adaptors was needed because costly restriction enzyme used later on in the process would be wasted in digesting the excess (as opposed to acting on the plasmid). Furthermore, even after routine purification or digestion with excess restriction enzymes, researchers were often still left with poly-linker inserts. With the present invention, since no restriction sites exist apart from the linked DNA, the restriction enzyme can attack only the desired area. Less enzyme is therefore required, or as in the alternative method, purification of excess linker is unnecessary.

Note also that when one uses the linkers of the present invention, one *always* preserves the amino acid (within the protein) that is adjacent to the insert (and often repeats it twice). Thus, distortions caused by loss of a previously coded for amino acid are minimized.

For example, when a six member "blunt end" double stranded adaptor

<u>CCGCGG</u>
<u>GGCGCC</u> is inserted in the middle of a codon in

CGT CGA CAG, to yield CGT C<u>CC GCG GG</u>A CAG,
Arg Arg His          ARG PRO ALA GLY HIS an ARG is replaced by PRO-ALA-GLY. On the other hand, if one of the present invention's linkers, TCGAGC, is inserted as follows CGT <u>CGA GCT</u> CGA CAG,
ARG ARG ALA ARG HIS the ARG is preserved.

Moreover, in over half of the 2 base overhangs and almost all of the 4 base overhangs the amino acid is repeated twice (on both sides of the linker). Further, given that the linker is a hexameric oligonucleotide which codes for exactly two amino acids (6/3=2), there is no frame shift caused by the insertion.

Another advantage of the linker is that because the insertion is so short and attaches using sticky ends, there is little tendency for the resulting plasmid to mutate out the linker. Thus, unlike point mutations plasmids modified by these linkers are normally quite stable, and are likely to be very useful in producing compounds like vaccines where "back" mutations must be avoided.

It is also important to note that six base insertions are not readily derived by mutagenesis, they often give temperature sensitive phenotypes, and they provide genetic markers. Further, such insertions can have great utility in gene engineering (e.g. domain replacement, fusion, deletion, and duplication).

The objects of the invention therefore include:
a. Providing a linker of the above kind which permits the insertion of selected restriction sites in non-blunt end tab sites without causing frame shifts.
b. Providing a linker of the above kind which inserts only one restriction enzyme recognition site.
c. Providing a linker of the above kind which does not destroy a pre-existing codon within a reading frame for all possible reading frames.
d. Providing a method for using such linkers which reduces the waste of restriction enzyme.

These and other objects and advantages of the invention will be apparent from the description which follows. This description does not represent the full scope of the invention. Rather, the invention may be employed in other embodiments. Thus, the claims should be looked to in order to define the scope of the invention.

DESCRIPTION OF THE PREFERRED EMBODIMENTS

A. Overview Of Synthesis Of Linkers

A detailed synthesis of three representative linkers is described in sections D, F and H below. The following oligodeoxynucleotides are chemically synthesized by the solution triester method. See generally G. R. Gough et al., 7 Nuclear Acids Research 1955 (1979); G. R. Gough et al. 23 Tetrahedron Letters 3439 (1982). The strategy is to use commercially available dimers so the hexamer synthesis is completed in two reaction cycles. These syntheses can easily be adapted to allow one skilled in the art to create the other linkers which fall within the scope of the invention.

Also, it should be noted that there are a number of well known procedures for producing eight and ten member double stranded oligonucleotides. One such method is called the "modified tri-ester method". See C. Bahl et al., 81 Biochemical And Biophysical Research Communications 695–703 (1978); See also J. Stawinski et al. 54 Canad. J. Chem 670–72 (1976) and 4 Nucleic Acid Res. 353–371 (1977). See also A. K. Sood et al. 4 Nucleic Acid Res. 2757–2765 (1977). Using analogous procedures, the hexameric oligonucleotides of the present invention can be produced.

B. Overview Of Use Of Linkers

Three examples of methods for using the linkers of the present invention are given below in sections E, G and I below. In more general terms, the preferred method can be summarized as follows:

1. First cut the gene sequence with a restriction enzyme at a point where a newly specified restriction site is to be inserted. Example: Treat a plasmid having a Sal I (and Acc I) site with Acc I at standard Acc I conditions:

... 5'-GT ..... CGAC-3' ...
... 3'-CAGC ..... TG-5' ...

2. Add the hexameric linkers with a ligase. Example: Use T4 ligase at the conditions as specified hereinafter (generally at lower than standard temperatures with a greater than normal amount of enzyme) and use the linker pCCAGCT (which inserts a Sac I site).

3. Recut using the restriction enzyme that the newly inserted site recognizes. Example: Recut with Sac I at standard Sac I conditions.

4. Dilute with ligase buffer and recircularize with ligase. Example: Use T4 ligase (or as an option add biological cassette in ligation reaction and go to step 6)

5. Enriching for desired plasmids. Example: Use standard biochemical selection techniques (recut with Sal I to enrich for plasmids containing linker).

6. Transform into cells.

In some cases, less steps are necessary. Also, it should be noted that it is preferred to use the 5'-OH end linker for most 3' overhang sites such as (GCG ..... C),
(C ..... GCG)

and the 5'-phosphate end linker for most 5' overhang sites such as (C . . . . . CGG)
(GGC . . . . . C).

C. Selection Of Appropriate Linkers

The list below gives details as to which linkers are known to be suitable to convert a given restriction site to another site. For a more complete list, there has been deposited in the U.S. Copyright Office an article prepared by the applicant that received registration number TXU 146-641.

For a given type of end, in the column headed "CONVERSION", the enzymes which are known to be capable of producing such an overhang are listed first. Isoschizomers and related enzymes are listed below in parentheses, with an asterisk indicating related enzymes which form the overhang on only some sites. The enzymes that recognize the new site are listed after the arrow, with related enzymes below in parentheses. Addition of the linker shown in the column "TAB LINKER" to the site creates the new restriction site. Additional conversions using the same linker are listed to the right of the linker in a similar format.

|  | CONVERSION | | TAB LINKER (5' → 3') | ADDITIONAL CONVERSIONS | | |
|---|---|---|---|---|---|---|
|  | 3' CG overhang | | | | | |
| (1) | Hha I (Cfo I) | → Eco RI | (AATTCG) | 5' AATT overhang Eco RI | → | Asu II |
| (2) | Hha I (Cfo I) | → Eco RV | (ATATCG) | | | |
| (3) | Hha I (Cfo I) | → Sac I (Ban II) | (AGCTCG) | 5' AGCT overhang Hind III | → | Xho I (Ava I) |
| (4) | Hha I (Cfo I) | → Sph I (Nsp CI) | (CATGCG) | 5' CATG overhang Nco I (Afl III*) | → | Mst I |
| (5) | Hha I (Cfo I) | → Nae I | (CCGGCG) | 5' CCGG overhang Xma I (Ava I*) | → | Nar I (Bde I) (Aha II) (Ban I) (Hae II) |
| (6) | Hha I (Cfo I) | → Bam HI (Xho II) | (GATCCG) | | | |
| (7) | Hha I (Cfo I) | → Nar I (Bde I) (Aha II) (Ban I) (Hae II) | (GCGCCG) | 5' GCGC overhang (Ban I*) | → | Nae I |
| (8) | Hha I (Cfo I) | → Apa I (Ban II) | (GGCCCG) | 5' GGCC overhang Xma III Not I Cfr I Gdi II | → | Xma I (Sma I) (Ava I) |
| (9) | Hha I (Cfo I) | → Kpn I | (GTACCG) | | | |
| (10) | Hha I (Cfo I) | → Sal I (Acc I) (Hinc II) | (TCGACG) | 5' TCGA overhang Sal I Xho I (Ava I*) | → | Aat II (Aha II) |
| (11) | Hha I (Cfo I) | → Aat II (Aha II) | (ACGTCG) | | | |
|  | 3' GC overhang | | | | | |
| (12) | Sac II | → Xma III (Not I) (Cfr I) (Gdi I) | (GGCCGC) | 5' GGCC overhang Xma III Not I Cfr I Gdi II | → | Sac II (Nsp BII) |
| (13) | Sac II | → Pvu I | (GATCGC) | 5' GATC overhang Bgl II Bam HI Xho II Bcl I Mbo I Sau IIA | → | Nru I |
| (14) | Sac II | → Nco I | (CATGGC) | 5' CATG overhang Nco I | → | Bal I (Cfr I) (Hae I) |
| (15) | Sac II | → Xma I (Sma I) (Ava I) | (CCGGGC) | 5' CCGG overhang Xma I (Ava I*) | → | Apa I (Ban II) |
| (16) | Sac II | → Nde I | (ATATGC) | | | |
| (17) | Sac II | → Pst I | (TGCAGC) | 5' TCGA overhang | | |

| | CONVERSION | | TAB LINKER (5' → 3') | ADDITIONAL CONVERSIONS | | |
|---|---|---|---|---|---|---|
| (18) | Sac II | → | Xho I (Ava I) | (TCGAGC) | Sal I Xho I (Ava I*) | → Sac I (Ban II) |
| | See also # 37, & # 40 | | | | | |
| | 5' CG overhang | | | | | |
| (19) | Hpa II | | | | | |
| | (Msp I) | | | | | |
| | HinPl I | | | | | |
| | (Sci NI) | | | | | |
| | Taq I | | | | | |
| | Cla I | | | | | |
| | Nar I | | | | | |
| | Aha II | | | | | |
| | Asu II | | | | | |
| | Acc I* | → | Eco RI | (CGAATT) | | |
| (20) | Hpa II | | | | | |
| | (Msp I) | | | | | |
| | HinPl I | | | | | |
| | (Sci NI) | | | | | |
| | Taq I | | | | | |
| | Cla I | | | | | |
| | Nar I | | | | | |
| | Aha II | | | | | |
| | Asu II | | | | | |
| | Acc I* | → | Eco RV | (CGATAT) | | |
| (21) | Hpa II | | | | | |
| | (Msp I) | | | | | |
| | HinPl I | | | | | |
| | (Sci NI) | | | | | |
| | Taq I | | | | | |
| | Cla I | | | | | |
| | Nar I | | | | | |
| | Aha II | | | | 3' AGCT overhang | |
| | Asu II | | | | | |
| | Acc I* | → | Sac I (Ban II) | (CGAGCT) | Sac I (Ban II*) | → Xho I (Ava I) |
| (22) | Hpa II | | | | | |
| | (Msp I) | | | | | |
| | HinPl I | | | | | |
| | (Sci NI) | | | | | |
| | Taq I | | | | | |
| | Cla I | | | | | |
| | Nar I | | | | | |
| | Aha II | | | | 3' CATG overhang | |
| | Asu II | | | | | |
| | Acc I* | → | Sph I (Nsp CI) | (CGCATG) | Sph I Nsp CI | → Mst I |
| (23) | Hpa II | | | | | |
| | (Msp I) | | | | | |
| | HinPl I | | | | | |
| | (Sci NI) | | | | | |
| | Taq I | | | | | |
| | Cla I | | | | | |
| | Nar I | | | | | |
| | Aha II | | | | | |
| | Asu II | | | | | |
| | Acc I* | → | Bam HI (Xho II) | (CGGATC) | | |
| (24) | Hpa II | | | | | |
| | (Msp I) | | | | | |
| | HinPl I | | | | | |
| | (Sci NI) | | | | | |
| | Taq I | | | | | |
| | Cla I | | | | | |
| | Nar I | | | | | |
| | Aha II | | | | 3' GGCC overhang | |
| | Asu II | | | | | |
| | Acc I* | → | Apa I (Ban II) | (CGGGCC) | Apa I (Ban II*) | → Xma I (Sma I) (Ava I) |
| (25) | Hpa II | | | | | |
| | (Msp I) | | | | | |
| | HinPl I | | | | | |
| | (Sci NI) | | | | | |
| | Taq I | | | | | |
| | Cla I | | | | | |
| | Nar I | | | | | |
| | Aha II | | | | | |
| | Asu II | | | | 3' GCGC overhang | |
| | Acc I* | → | Nar I | (CGGCGC) | Bde I | → Nae I |

|  | CONVERSION | | TAB LINKER (5' → 3') | ADDITIONAL CONVERSIONS | | |
|---|---|---|---|---|---|---|
| | | (Aha II) | | Hae II | | |
| | | (Bde I) | | | | |
| | | (Ban I) | | | | |
| | | (Hae II) | | | | |
| (26) | Hpa II | | | | | |
| | (Msp I) | | | | | |
| | HinPl I | | | | | |
| | (Sci NI) | | | | | |
| | Taq I | | | | | |
| | Cla I | | | | | |
| | Nar I | | | | | |
| | Aha II | | | | | |
| | Asu II | | | | | |
| | Acc I* | → Kpn I | (CGGTAC) | | | |
| (27) | Hpa II | | | | | |
| | (Msp I) | | | | | |
| | HinPl I | | | | | |
| | (Sci NI) | | | | | |
| | Taq I | | | | | |
| | Cla I | | | | | |
| | Nar I | | | | | |
| | Aha II | | | | | |
| | Asu II | | | | | |
| | Acc I* | → Sal I | (CGTCGA) | | | |
| | | (Acc I) | | | | |
| | | (Hinc II) | | | | |
| (28) | Hpa II | | | | | |
| | (Msp I) | | | | | |
| | HinPl I | | | | | |
| | (Sci NI) | | | | | |
| | Taq I | | | | | |
| | Cla I | | | | | |
| | Nar I | | | | | |
| | Aha II | | | | | |
| | Asu II | | | | | |
| | Acc I* | → Aat II | (CGACGT) | 3' ACGT overhang | | |
| | | (Aha II) | | Aat II | → | Sal I |
| | | | | | | (Acc I) |
| | | | | | | (Hinc II) |
| (29) | Hpa II | | | | | |
| | (Msp I) | | | | | |
| | HinPl I | | | | | |
| | (Sci NI) | | | | | |
| | Taq I | | | | | |
| | Cla I | | | | | |
| | Nar I | | | | | |
| | Aha II | | | | | |
| | Asu II | | | | | |
| | Acc I* | → Nae I | (CGCCGG) | | | |
| | 5' TA overhang | | | | | |
| (30) | Nde I | → Mlu I | (TACGCG) | | | |
| (31) | Nde I | → Cla I | (TATCGA) | | | |
| | See also # 38, 50, 51, and 52. | | | | | |
| | 3' GGCC overhang | | | | | |
| (32) | Apa I | | | 5' AT overhang | | |
| | (Ban II*) | → Nco I | (ATGGCC) | Acc I* | → | Bal I |
| (33) | Apa I | | | | | |
| | (Ban II*) | → Sac II | (GCGGCC) | | | |
| | | (Nsp BII) | | | | |
| | See also # 24 and 51 | | | | | |
| | 5' TCGA overhang | | | | | |
| (34) | Sal I | | | 3' AT overhang | | |
| | Xho I | | | Pvu I | → | Asu II |
| | (Ava I*) | → Eco RI | (TCGAAT) | | | |
| (35) | Sal I | | | | | |
| | Xho I | | | | | |
| | (Ava I*) | → Eco RV | (TCGATA) | | | |
| | See also # 10 and 18. | | | | | |
| | 5' CGCG overhang | | | | | |
| (36) | Mlu I | | | 3' AT overhang | | |
| | (Afl III*) | | | Pvu I | → | Nru I |
| | Bss HII | → Pvu I | (CGCGAT) | | | |
| (37) | Mlu I | | | | | |
| | (Afl III*) | | | | | |
| | Bss HII | → Xma III | (CGCGGC) | | | |
| | | (Not I) | | | | |
| | | (Cfr I) | | | | |
| | | (Gdi II) | | | | |
| | 3' TGCA overhang | | | | | |
| | | | | 5' TA overhang | | |

| CONVERSION | | | TAB LINKER (5' → 3') | ADDITIONAL CONVERSIONS | | |
|---|---|---|---|---|---|---|
| (38) | Pst I | → Nde I | (TATGCA) | Nde I | → | AVA III |
| (39) | Pst I | → Pvu II (Nsp BII) | (GCTGCA) | | | |
| 5' AGCT overhang | | | | | | |
| | | | | 3' GC overhang | | |
| (40) | Hind III | → Pst I | (AGCTGC) | Sac II | → | Pvu II (Nsp BII) |
| See also #3 | | | | | | |
| 3' AGCT overhang | | | | | | |
| (41) | Sac I | → Pst I | (GCAGCT) | | | |
| See also # 21 | | | | | | |
| 5' CCGG overhang | | | | | | |
| (42) | Xma I (Ava I*) | → Bam HI (Xho II) | (CCGGAT) | | | |
| (43) | Xma I (Ava I*) | → Kpn I | (CCGGTA) | | | |
| See also # 5, and # 15 | | | | | | |
| 3' GTAC overhang | | | | | | |
| (44) | Kpn I | → Mlu I | (GCGTAC) | | | |
| 3' GCGC overhang | | | | | | |
| (45) | Bde I Hae II | → Sph I (Nsp CI) | (ATGCGC) | 5' AT overhang Acc I* | → | Mst I |
| See also # 25 | | | | | | |
| 5' GGCC overhang | | | | | | |
| (46) | Xma III Not I Cfr I Gdi II | → Nco I | (GGCCAT) | 3' AT overhang Pvu I | → | Bal I (Cfr I) (Hae I) |
| See also # 8 and # 12 | | | | | | |
| 3' AT overhang | | | | | | |
| (47) | Pvu I | → Mst I | (GCGCAT) | 5' GCGC overhang (Ban I*) | → | Sph I (Nsp CI) |
| See also # 34, # 36, # 46, and # 49 | | | | | | |
| 5' GATC overhang | | | | | | |
| (48) | Bgl II Bam HI Xho II Bcl I Mbo I Sau IIIA | → Xba I | (GATCTA) | | | |
| 3' AT overhang | | | | | | |
| | | | | 5' CTAG overhang | | |
| (49) | Pvu I | → Xba I | (CTAGAT) | Xba I | → | Bgl II (Xho II) |
| 5' ↓TA overhang | | | | | | |
| (50) | Nde I | → Bgl II | (TAGATC) | | | |
| | | | | 3' GGCC overhang | | |
| (51) | Nde I | → Stu I (Hae I) | (TAGGCC) | Apa I (Ban II*) | → | Avr II |
| (52) | Nde I | → Sca I | (TAGTAC) | | | |

Linkers 48–52 are also useful in converting an open reading frame to a possible amber mutation (m-RNA containing a UAG sequence).

D. Example I-A—Synthesis Of Linker Useful For 4-base-5' Overhang

Single stranded TCGAGC (DNA) (linker 18) was synthesized as follows:

Cycle 1. Coupling Reaction to Lengthen Chain

To 2.83 mg of $N^2$-isobutyryl-2'-deoxyguanosine-3'-(p-chlorophenyl)phosphate-5'-$N^4$-benzoyl-3'-O'benzoyl-2'-deoxycytidine is added 4.59 mg of 5'-O-dimethoxytrityl-$N^2$-isobutyryl-2'-deoxyguanosine-3'-(p-chlorophenyl)phosphate-5'-$N^6$-benzoyl-2'-deoxyadenosine-3'-(p-chlorophenyl)phosphate, triethylammonium salt. The mixture is dissolved in 0.15 ml of dry pyridine, the solution evaporated to a thick syrup, 0.15 ml of dry pyridine added and the solution is again evaporated to a thick syrup. The pyridine additions and evaporations are done a total of four times. Three milligrams of 1-(p-toluenesulfonyl)-3-nitro-1,2,4-triazole dissolved in 0.010 ml of dry pyridine is added to the final syrup. The mixture is allowed to stand at a temperature greater than 30 degrees centigrade for one hour.

At one hour 1 ml of chloroform is added. This solution is extracted with 0.5 ml of 5% sodium bicarbonate/tertiary butyl alcohol, 80/20 (v/v) by shaking on a vortex mixer and centrifuging to separate into two layers. Discard the upper layer and extract the chloroform layer with 0.5 ml of tertiary butyl alcohol/distilled water, 10/90 (v/v) by shaking on a vortex mixer and centrifuging to separate into two layers. Discard the upper layer. The chloroform layer is concentrated to 0.1 ml and precipitated with 1.4 ml diethyl ether. The precipitate is air dried, dissolved in 0.1 ml of chloroform/methanol, 70/30 (v/v) and cooled to 4 degrees centigrade. Add 0.075 ml of an 8% (w/v) benzenesulfonic acid in chloroform/methanol, 70/30 (v/v) solution (precooled to 4 degrees centigrade). After 6 minutes add 0.020 ml of pyridine.

This solution is extracted with 0.5 ml of 5% sodium bicarbonate/tertiary butyl alcohol, 80/20 (v/v) by shaking on a vortex mixer and centrifuging to separate into two layers. Discard the upper layer and extract the chloroform layer with 0.5 ml of tertiary butyl alcohol/distilled water, 10/90 (v/v) by shaking on a vortex mixer and centrifuging to separate into two layers. Discard the upper layer. The chloroform layer is concentrated to 0.1 ml, precipitated with 1.4 ml of diethyl ether and air dried.

Cycle 2. Further Chain Elongation

The final air dried precipitate from cycle one is dissolved in 0.15 ml of dry pyridine and 3.79 mg of 5'-O-dimethoxytrityl-2'-deoxythymidine 3'-(p-chlorophenyl)phosphate-5'-N$^4$-benzoyl 2'-deoxycytidine 3'-(p-chlorophenyl)phosphate, triethylammonium salt is added. The solution is evaporated to a thick syrup, 0.15 ml of dry pyridine is added and again evaporated to a thick syrup. The pyridine additions and evaporations are done a total of 4 times. Three milligrams of 1-(p-toluenesulfonyl)-3-nitro-1,2,4-triazole dissolved in 0.010 ml of dry pyridine is added to the final syrup. The mixture is allowed to stand at a temperature greater than 30 degrees centigrade for one hour.

At one hour 1 ml of chloroform is added. This solution is extracted with 0.5 ml of 5% sodium bicarbonate/tertiary butyl alcohol, 80/20 (v/v) by shaking on a vortex mixer and centrifuging to separate into two layers. Discard the upper layer and extract the chloroform layer with 0.5 ml of tertiary butyl alcohol/distilled water, 10/90 (v/v) by shaking on a vortex mixer and centrifuging to separate into two layers. Discard the upper layer. The chloroform layer is concentrated to 0.1 ml and precipitated with 1.4 ml of diethyl ether. The precipitate is air dried.

Deprotection

The final ether precipitate is dissolved in 0.25 ml of oximate (C. B. Reese et al. Tetrahedron Letters 2727 (1978)) solution (1M 2-pyridinealdoxime and 1M 1,1,3,3-tetramethylguanidine in 50% aqueous dioxane). This is incubated at 37 degrees centigrade for 24 hours. Ten milliliters of ammonium hydroxide and 0.75 ml of pyridine are added. This is incubated in a sealed flask at 50 degrees centigrade for 24 hours.

After 24 hours the above solution is concentrated to a syrup. Ten milliliters of distilled water are added and the solution is concentrated to a syrup. A second 10 ml of distilled water is added and the solution is concentrated to a syrup. The syrup is dissolved in 10 ml of acetic acid/water, 80/20 (v/v) and allowed to stand at room temperature for twenty minutes. After twenty minutes the solution is concentrated to a syrup. Ten milliliters of distilled water are added and the solution is concentrated to a syrup. A second 10 ml of distilled water is added and the solution is concentrated to a syrup.

The syrup is dissolved in 3 ml of distilled water and extracted three times with 2 ml of diethyl ether by shaking on a vortex mixer and centrifuging to separate into two layers. The ether layer (upper) is discarded each time. The water layer is then extracted 4 times with 2 ml of n-butyl alcohol/distilled water 5/1 (v/v) by shaking on a vortex mixer and centrifuging to separate into two layers. The n-butyl alcohol layer (upper) is discarded each time. The water layer is concentrated to 0.15 ml.

Purification

The oligomer 5'-d(TCGAGC)-3' is purified by preparative polyacrylamide gel electrophoresis. The gel is 33×30×0.3 cm. The composition is 20% acrylamide, 1% bisacrylamide, 7M urea, 0.1M tris-borate pH 8.3 and 0.02M EDTA. Add 0.455 ml of 10M urea, 0.002 ml of 0.4% bromophenol blue (w/v) and 0.006 ml of 1.0M tris-borate pH 8.3+0.02M EDTA to the oligodeoxynucleotide solution from deprotection. This is applied to three 8 cm long wells in the gel. Electrophoresis is carried out at 250 to 350 volts until the bromophenol blue dye has migrated 25 to 30 cm (approximately 16–20 hours).

The oligodeoxynucleotides are viewed by UV shadowing, and the bands are cut out of the gel. They are homogenized in a solution of 0.1M NaCl and 0.01M tris-Cl pH 8.0. The homogenate is allowed to stand at room temperature for 1 hour, the acrylamide is filtered off and the oligodeoxynucleotide absorbed to Sephadex ®A-25. The Sephadex ®A-25 is washed with a solution of 0.1M NaCl and 0.02M tris-Cl pH 8.0 and the oligodeoxynucleotide is eluted with a solution of 1.0M NaCl and 0.02M sodium acetate pH 5.5. The oligodeoxynucleotide is absorbed on a Waters Mu Bondapak C-18 reverse phase column, the column is washed with water and the oligodeoxynucleotide is eluted with acetonitrile/water, 40/60 (v/v). The oligodeoxynucleotide is concentrated to 75 A$_{260}$ units/ml and freeze-dried.

Analysis

The oligodeoxynucleotide is checked for purity by labeling with $\gamma^{32}$ p-ATP using polynucleotide kinase followed by analytical gel electrophoresis. The sequence is confirmed by modified Maxam-Gilbert sequencing. A Maxam et al. 65 Methods Enzymol. 449 (1980); A. M. Banaszuk et al. 128 Analytical Biochem. 281 (1983).

E. Example I-B—Insertion of TCGAGC Linker Into 4-Base-5' Overhang Site

Plasmid pKP772 is a derivative of pBR322 (from *E. coli*) that has about 1,200 bp deleted between the end of the tetracycline resistance gene and the origin of replication. This plasmid was generously provided by Keith Peden. Plasmid pFB69 is a derivative of pKP772 that was created by applicant, where the Eco RI site was filled in, and a Xho I-Bgl II-Xho I linker was inserted at that site. It was chosen as a suitable DNA sequence which had a selected tab site of interest. However, numerous other tab sites (or starting DNA) could have been chosen as examples. The primary reason for choosing pFB69 was that it had a Sal I site within the tetracycline resistance gene which provided a 4-base 5' overhang when treated with Sal I.

Conversion Of Sal I Site to Sac I

The single-stranded oligonucleotide TCGAGC was phosphorylated using kinase. 0.2 A260 OD units (approximately 8 Mu g) oligonucleotide in a total volume of 20 Mu l of 50 mM Tris-HCl pH 8.0 containing 10 mM MgCl$_2$, 1 mM EDTA, 6 mM mercaptoethanol, and 1 mM ATP (Kin-Lig Buffer) was phosphorylated with 7.5 U T4 polynucleotide kinase by incubating at 37° C.

for 2 hrs. The reaction was terminated by heat inactivation at 65° C. for 5 min.

Phosphorylated linker (0.1 A260 OD units (approx. 4 Mu g) was ligated to 0.5 Mu g Sal I linear pFB69 in 50 Mu l Kin-Lig Buffer using 5(Weiss) U T4 ligase at 4° C. overnight. Under these conditions approximately 80% of the plasmid remained in the linear form, with linker(s) at the ends.

Ligation was terminated by heating to 65° C. (5 min) and excess linker removed from ends by digestion with 15 U Sac I at 37° C. for 1 hr. DNA was precipitated by addition of 2 Mu l 0.5M EDTA, 2 Mu g yeast tRNA (carrier), 5 Mu l 3M sodium acetate and 3 volumes (160 Mu l) cold ethanol. The pellet was dissolved in 8 microliters 10 mM Tris-HCL pH 8.0 containing 1 mM EDTA (TE). Linear molecules were resolved by electrophoresis in 1% low melting agarose in 0.2M Tris-Glycinate buffer containing 1 Mu g/ml ethidium bromide at 80 V for 1 hr. The linear band was excised, an equal volume TE added, and the agarose melted at 65° C. for 5 min. DNA was purified from the agarose by 3 extractions with equal volume phenol, 2 extractions with equal volume butanol, and 2 ethanol precipitations (2 Mu g tRNA added as carrier).

The DNA was dissolved in 200 Mu l Kin-Lig Buffer, and linears circularized by ligation with 5 U T4 ligase at 16° C. overnight. Ligation was terminated by heating to 65° C. for 5 min, and nucleic acids precipitated by addition of 10 Mu l 0.5M EDTA, 20 Mu l 3M sodium acetate and 0.7 ml cold ethanol. The precipitate was washed with ethanol, and resuspended in 20 Mu l Te.

To enrich for DNA which had linkers, circular molecules which did not contain linker were linearized by digestion with Sal I (20 U enzyme in 40 Mu l 10 mM Tris-HCl pH 8.0 containing 150 mM NaCl, 10 mM MgCl$_2$, and 6 mM mercaptoethanol (high salt buffer) at 37° C. for 1 hr.) Since linear plasmid transforms E. coli several orders of magnitude less efficiently than circular DNA, this step (known as biochemical selection) enriches for transformants of plasmids containing the linker. (Linker containing plasmids are not cut by Sal I and remain circular).

DNA was ethanol precipitated and resuspended in 20 Mu l TE. 5 Mu l (about 50 ng) was used for transformation into frozen competent E. coli MM294 as described by D. Hanahan 166 J. Molecular Biology 557–580 (1983). Twelve ampicillin resistant clones were screened for the presence of a Sac I site by digestion of plasmids prepared from 3 ml cultures by the procedure of D. S. Holmes et al. 114 Anal. Biochem. 193–197 (1981). Ten were shown to contain a single Sac I site (no additional Xho I site) and had lost the Sal I site. The remaining two were the starting plasmid. One such plasmid containing a Sac I site within the Sal I site of pFB69 was designated pFBI2. Despite the insertion of 6 nucleotides, the gene still codes for tetracycline resistance.

In connection with this procedure, it should be noted that purification of plasmid from linker (via LM agarose, passing over a column, or centrifugation) may be necessary when using tandem duplications of hexameric linkers, such as a dodecamer with a 2 base or 4 base overhang. If biochemical selection is used, purification of plasmid may not be necessary.

For example, 0.1 A260 OD units (4 Mu g) pTCGAGC was ligated to 0.5 Mu g Sal I linear pFB69 using 5 U T4 ligase in 20 Mu l Kin-Lig buffer at 4° C. for 17 hours. After terminating the ligation (65° C. for 5 min) the reaction was diluted to 40 Mu l 10 mM Tris-HCL pH 8.0 containing 10 mM MgCl$_2$, and 6 mM mercaptoethanol (low salt buffer) and excess linker removed by incubation with 15 U Sac I at 37° C. for 1 hr. After removal of aliquots for gel analysis, the remaining 300 ng plasmid was ethanol precipitated as described above.

The precipitate was washed with ethanol and resuspended in 200 Mu l Kin-Lig buffer. DNA was ligated overnight at 16° C. with 5 U T4 ligase. After heat inactivating the ligase, nucleic acids were precipitated and washed with ethanol as described above. DNA was resuspended in 50 Mu l high salt buffer and molecules which did not contain linker were linearized with Sal I (20 U). The DNA was ethanol precipitated and resuspended in 20 Mu l TE. 100 ng plasmid was used for transformation into MM294 as described above. Ampicillin resistant clones: Sal I linear DNA with linker=$6.6\times10^4$, (pFBI2); Sal I linear DNA without linker=$1.6\times10^3$ (pFB69).

F. Example II-A—Synthesis Of Linker Useful For 2-Base-5′ Overhang

Single stranded pCGAGCT (linker 21) was synthesized as follows:

Cycle 1. Coupling Reaction To Lengthen Chain

To 2.55 mg of N$^4$-benzoyl-2′-deoxycytidine 3′-(p-chlorophenyl)phosphate-5′-3′-O-benzoyl-2′deoxythymidine is added 4.59 mg of 5′-O-dimethoxytrityl-N$^6$-benzoyl-2′-deoxyadenosine 3′-(p-chlorophenyl)phosphate-5′-N$^2$-isobutyryl-2′-deoxyguanosine 3′-(p-chlorophenyl)phosphate, triethylammonium salt. Cycle 1 is continued and completed exactly as described in Example I-A.

Cycle 2. Further Chain Elongation

The final air dried precipitate from cycle 1 is dissolved in 0.15 ml of dry pyridine and 4.06 mg of 5′-O-dimethoxytrityl-N$^4$-benzoyl-2′-deoxycytidine 3′-(p-chlorophenyl)phosphate-5′-N$^2$-isobutyryl-2′-deoxyguanosine 3′-(p-chlorophenyl)phosphate, triethylammonium salt is added. Cycle 2 is continued and completed exactly as described in cycle 1, Example I-A.

Cycle 3. Ribonucleotide Addition

The final air dried precipitate from cycle 2 is dissolved in 0.15 ml of dry pyridine and 1.81 mg of 2′,3′-dibenzoyluridine 5′-(p-chlorophenyl)phosphate, barium salt is added. Cycle 3 is continued and completed exactly as described in cycle 2, Example I-A.

Deprotection

The final ether precipitate is dissolved in 0.25 ml of oximate solution (1M 2-pyridinealdoxime and 1M 1,1,3,3-tetramethylguanidine in 50% aqueous dioxane). This is incubated at 37 degrees centigrade for 24 hours. Ten milliliters of ammonium hydroxide and 0.75 ml of pyridine are added. This is incubated in a sealed flask at 50 degrees centigrade for 24 hours.

After 24 hours the above solution is concentrated to a syrup. Ten milliliters of distilled water are added and the solution is concentrated to a syrup. A second 10 ml of distilled water is added and the solution is concentrated to a syrup.

The syrup is dissolved in 3 ml of distilled water and extracted three times with 2 ml of diethyl ether by shaking on a vortex mixer and centrifuging to separate into two layers. The ether layer (upper) is discarded each time. The water layer is then extracted 4 times with 2 ml of n-butyl alcohol/distilled water, 5/1 (v/v) by shaking on a vortex mixer and centrifuging to separate into two layers. The n-butyl alcohol layer (upper) is discarded each time. The water layer is concentrated to 0.15 ml.

Purification

The oligodeoxynucleotide is purified exactly as described in Example I-A purification.

Deprotection Of 5'-Phosphate

The freeze-dried oligodeoxynucleotide is dissolved in 0.6 ml of a solution of 0.5M sodium glutamate and 1.0M cyclohexylamine. Add 0.5 ml of 0.1M NaIO$_4$ and incubate for 0.5 hour at 45 degrees centigrade. Add 0.5 ml of 0.4M D-ribose to the oligodeoxynucleotide solution and absorb to Sephadex®A-25. The Sephadex®A-25 is washed with a solution of 0.1M NaCl and 0.02M tris-Cl pH 8.0 and the oligodeoxynucleotide is eluted with a solution of 1.0M NaCl and 0.02M sodium acetate pH 5.5. The oligodeoxynucleotide is absorbed on a Waters Mu Bondapak®C-18 reverse phase column, the column is washed with water and the oligodeoxynucleotide is eluted with acetonitrile/water, 40/60 (v/v). The oligodeoxynucleotide is concentrated to 75 $A_{260}$ units/ml and freeze-dried.

Analysis

The oligodeoxynucleotide pd(CGAGCT) is analyzed exactly as described in the Example I-A analysis.

G. Example II-B—Insertion Of pCGAGCT Linker Into 2-Base 5' Overhang Site

Conversion of pFB69 Acc I site within the tetracycline resistance gene to Sac I

The following experiment demonstrates that there is a preferred linker concentration for the single tube ligation procedure. Tubes designated A–F contained 0.5 Mu g Acc I linear pFB69 in 10 Mu l Kin-Lig buffer, and 0, 0.5, 1.0, 2.0, 4.0, and 8.0 Mu g pCGAGCT linker respectively. Ligation of linker to plasmid was initiated by addition of 4.5 U T4 ligase at 16° C. and terminated 1 hr later by heating to 65° C. for 5 min. 100 ng plasmid (2 Mu l) aliquots were removed and DNA conformers analyzed by electrophoresis in 1% agarose gels. DNA from tube A (no linker) was approximately 80% multimers, 15% linear monomer, and 5% monomercircle; from tube D (2 Mu g linker)—40% multimers, and 60% linear monomer; from tube F (8 Mu g linker)—10% dimer, 90% linear monomer, and a smear of polylinker was visible (to about 2 kb).

The samples were diluted to 40 Mu l in low salt buffer and excess linker removed by digestion with 15 U Sac I at 37° C. for 1 hr. Analysis of 100 ng (10 Mu l) DNA revealed: Tube A—DNA unchanged; tube D—5% multimers and 95% linear monomer; tube F—100% linear monomer and polylinker smear reduced to oligolinker size. The remaining 30 Mu l was diluted to 50 Mu l containing 20 mM EDTA, and extracted once with phenol, and twice with n-butanol. Nucleic acids were precipitated by addition of 2 Mu g tRNA, 5 Mu l 3M sodium acetate and 165 Mu l cold ethanol. The precipitates were washed with ethanol and resuspended in 200 Mu l Kin-Lig buffer.

DNA was ligated by addition of 4.5 U T4 ligase at 16° C. for 17 hr. Ligation was terminated by heating to 65° C. for 5 min. Nucleic acids were precipitated by addition of 10 Mu l 0.5M EDTA, 20 Mu l 3M sodium acetate and 0.65 ml cold ethanol. The precipitates were washed with ethanol and resuspended in 30 Mu l TE. Analysis of 100 ng DNA (10 Mu l) by electrophoresis revealed some ligation to give multimers and circular monomers. The remaining 20 Mu l were diluted to 40 Mu l high salt buffer and resealed starting plasmid linearized by digestion with 20 U Sal I at 37° C. for 1 hr. (Biochemical selection step). Nucleic acids were precipitated by addition of 2 Mu l 0.5M EDTA, 18 Mu l H$_2$O, 6 Mu l 3M sodium acetate and 200 Mu l cold ethanol. The precipitates were washed with ethanol, resuspended in 20 Mu l TE, with 10 Mu l (100 ng) used for gel analysis, and the remaining 100 ng used for transformation (See Table 1).

Analysis of the DNA conformers after the final step revealed: tube A and B—approximately 5% multimers and 95% linear monomers; tube C, D, and E—20% oligomers, 75% linear monomers, and from 2–5% monomer circles; and tube F—95% linear monomers.

TABLE 1

| Tube | pCGAGCT Linker A260 OD | Amp$^R$ Transformants$^a$ | Tet$^R$ Transformants$^a$ |
|---|---|---|---|
| A | 0 | 2.2 × 10$^3$ | 1.6 × 10$^{3b}$ |
| B | .0125 | 3.0 × 10$^3$ | 3.2 × 10$^3$ |
| C | .025 | 4.7 × 10$^4$ | 2.9 × 10$^{4c}$ |
| D | .05 | 5.9 × 10$^4$ | 3.6 × 10$^{4c}$ |
| E | .1 | 2.3 × 10$^4$ | 1.6 × 10$^{4c}$ |
| F | .2 | 5.4 × 10$^3$ | 2.8 × 10$^3$ |

$^a$100 ng DNA was used for transformation of 0.2 ml frozen competent MM294 E. coli as described above. After 1.5 hr expression, cells were diluted and spread on plates containing 50 mug/ml ampicillin or 15 mug/ml tetracycline. Efficiency of plating is slightly higher on ampicillin than on tetracycline.
$^b$Transformants contain starting plasmid.
$^c$Most transformants contain a Sac I site within the Acc I (Sal I) site of pFB69.

From the above data the optimal linker concentration for pCGAGCT ligation (to 0.5 Mu g Acc I linear pFB69) is from 0.025–0.05 A260 OD units (1–2 Mu g) in 10 Mu l at 16° C. Optimal conditions for other linkers have been determined, and vary in both concentration and ligation temperatures. If biological selection is required, a cassette containing Sac I ends is added during the second ligation, and the biochemical selection step ommited.

For insertion of tandem duplicate pCGAGCT linker, 2 Mu g linker was ligated to 0.5 Mu g pKP772 as described above. Instead of removing excess linker with Sac I, 20 U Xho I was used (in high salt buffer), with the remaining reactions as described above. Of 4 ampicillin resistant clones examined, all contained plasmids with Sac I-Xho I-Sac I in the Acc I site (designated pFBI15), and all retained the ability to code for tetracycline resistance.

H. Example III-A—Synthesis Of Linker Useful For 2-Base 3' Overhang

Single stranded AATTCG (Linker 1) was synthesized as follows:

Cycle 1. Coupling Reaction To Lengthen Chain

To 2.83 mg of N$^4$-benzoyl-2'-deoxycytidine 3'-(p-chlorophenyl)phosphate-5'-N$^2$-isobutyryl-3'-O-benzoyl 2'-deoxyguanosine is added 3.93 mg of 5'-O-dimethoxytrityl-2'-deoxythymidine 3'-(p-chlorophenyl)phosphate-5'-2'-deoxythymidine 3'-(p-chlorophenyl)phosphate, triethylammonium salt. Cycle 1 is continued and completed as described in Example I-A.

Cycle 2. Further Chain Elongation

The final air dried precipitate from cycle 1 is dissolved in 0.15 ml of dry pyridine and 4.17 mg of 5'-O-dimethoxytrityl-N$^6$-benzoyl-2'-deoxyadenosine 3'(p-chlorophenyl)phosphate-5'-N$^6$-benzoyl-2'-deoxyadenosine 3'-(p-chlorophenyl)phosphate, triethylammonium salt is added. Cycle 2 is continued and completed exactly as described in cycle 2, Example I-A.

Deprotection

The oligodeoxynucleotide 5'd(AATTCG)-3' is deprotected exactly as described in Example I-A deprotection.

Purification

The oligodeoxynucleotide 5'-d(AATTCG)-3' is purified exactly as described in Example I-A purification.

Analysis:

The oligodeoxynucleotide 5'-d(AATTCG)-3' is analyzed exactly as described in Example I-A analysis.

I. Example III-B—Insertion Of AATTCG Linker Into 2-Base 3' Overhang

Conversion of pFB69 Hha I sites within the ampicillin resistance gene to Eco RI

It was determined empirically that digestion of 30 Mu g pFB69 in 300 Mu l Kin-Lig buffer containing 75 Mu g/ml ethidium bromide with 8 U Hha I for 30 min at 37° C. converted about 75% to open circles and about 25% to linear monomers. Hha I linear pFB69 was purified from low melting agarose as described above. Non-phosphorylated linker AATTCG 0.1 A260 OD units (approx. 4 Mu g), was ligated to 0.5 Mu g Hha I linear pFB69 using 5 U T4 ligase in 10 Mu l Kin-Lig buffer at 4° C. for 17 hr. Ligation was terminated by heating to 65° C. for 5 min.

Analysis of 100 ng DNA by gel electrophoresis revealed that about 30% of the plasmid was multimeric, and 70% remained linear, with some molecules containing a single linker on each end. The remaining DNA was divided into 2×200 ng portions, one of which was phosphorylated with 5 U T4 kinase in 10 Mu l Kin-Lig buffer at 37° C. for 2 hr. Both portions were diluted into 100 Mu l Kin-Lig buffer containing 500 ng of purified kanamycin resistance cassette (with EcoRI sticky ends) from pUC4K (See J. Vieira et al., 19 Gene 259-268 (1982)) 5 U T4 Ligase, and incubated at 16° C. for 18 hr. Nucleic acids were ethanol precipitated as described above, and resuspended in 20 Mu l TE. Analysis of 100 ng DNA by gel electrophoresis revealed several ligation products.

The remaining 100 ng were used for transformation as described above, and transformants were selected on ampicillin-kanamycin and tetracycline-kanamycin plates. Without phosphorylation of linker the yield of clones was $1.6 \times 10^3$ Amp$^R$ Kan$^R$, and $1.4 \times 10^2$ Tet$^R$Kan$^R$; with phosphorylation the yield was $8.8 \times 10^3$ Amp$^R$Kan$^R$, and $2.6 \times 10^3$ Tet$^R$Kan$^R$ clones. About 40% of the Tet$^R$Kan$^R$ clones were Amp$^S$, indicating the cassette (with Eco RI ends) was within the ampicillin resistance gene.

Analysis of plasmid prepared from 20 Tet$^R$Kan$^R$Amp$^S$ clones gave at least two plasmids with the kanamycin resistance cassette in each of the three Hha I sites. The cassettes were removed by digestion with Eco RI; plasmids circularized with T4 ligase, and re-transformed into E. coli. Twelve clones of each plasmid were analyzed for resistance to various beta lactams.

Plasmid pFB15 contains an Eco RI site in Hha I at bp 3927 (pBR322 numbering, K. Peden, 22 Gene 277-280 (1983)) and is Amp$^S$. Plasmid pFBI3 contains an Eco RI site in Hha I at bp 3590 and is Amp$^S$. Plasmid (pFBI4) contains an Eco RI site in Hha I at bp 3497, and is Amp$^R$, but sensitive to 1 mg/ml ampicillin at 42° C. (Ts). Digestion of these plasmids with Hha I revealed a loss of Hha I sites in each of the above positions.

Using an unphosphorylated linker by the above "short" method works when converting a two base-3' overhang site into a four base-5' overhang site. The linker ligates to the 5' phosphate of the plasmid and leaves a four base 5' overhang, which is ready for ligating onto a four base 5' overhang cassette. For conversion of a 3' overhang to another 3' overhang site, a procedure analogous to Method II is used.

For all methods, for linearization of a plasmid with more than one restriction site, a number of alternatives exist. For example, it has been experimentally determined that incubation of 5 Mu g pKP772 with 12 U Hha I methylase in 50 Mu l 50 mM Tris-HCl pH 8.0 containing 10 mM EDTA, 230 MuM S-Adenosyl methionine, and 6 mM mercaptoethanol (Meth buffer) for 30 min at 37° C. gives nearly complete methylation. Subsequent digestion of this DNA with Hha I yields about one third linear monomers, completely or hemi-methylated at all other Hha I sites. Such linears may be used with the biochemical selection or cassette methods described above. Methylation conditions with Taq I methylase and Hpa II methylase have also been determined.

In addition, a plasmid may be methylated to completion with Hha I methylase. Digestion of the plasmid under non-standard conditions could linearize the plasmid at degenerate sequences other than Hha I sites. Linkers could be inserted into linear plasmids with 3' CG overhangs as described in Method III.

Thus, it can be seen that the present invention has inter alia the following advantages:

1. A given linker can be used on both 5' and 3' sticky ends.
2. It only forms a new restriction site upon addition to double stranded DNA.
3. It is a simple technique for insertion of only a single restriction site.
4. The reaction can be completed in a single tube, without purifying away excess linker.
5. Insertion of the two codons never destroys an adjacent preexisting codon.
6. For most 2 base overhang, and for virtually all 4 base overhang linker insertions, a coded amino acid within the original reading frame is repeated on both sides of a newly coded amino acid after insertion of the linker.
7. It permits two codon insertion without causing a frame shift.
8. The nature of inserted amino acids can be changed by using alternative single stranded linkers.
9. These linkers are compatible with biochemical or biological selection techniques.
10. Several mutations at essentially predetermined sites can be obtained.
11. The site of mutation can be determined by simple restriction digests. Changes in amino acids can be determined without sequencing DNA.
12. Only a single mutation is made in a gene.

Although the especially preferred embodiments of the invention has been described above, it should be noted that the invention is not so limited. In this regard, there may be various other modifications and changes in these embodiments which are within the scope of the invention. For example, it is not necessary that DNA linkers be used. RNA linkers are also of interest. Of course, for RNA the sequences will typically use "U" as a base. Such modifications and other modifications are meant to be within the scope of the invention. The invention is therefore not to be limited by the illustrative description above.

I claim:

1. A method for inserting a selected restriction site into a double stranded genetic sequence at a selected tab site comprising:

treating a double stranded DNA genetic sequence with a type II restriction enzyme that cleaves both strands at a selected tab site and produces complementary single stranded termini on each strand of said genetic sequence;

exposing said cleaved genetic sequence to two hexameric single stranded DNA oligonucleotide linkers in the presence of a ligating enzyme, wherein said linkers have the same nitrogenous base sequence, and wherein said linker sequence is palindromic complementary to both ends of said linker sequence with respect to only either two or four bases per end and wherein said linker sequence is a recognition site for a restriction enzyme; and selecting said genetic sequence, wherein said linker sequence has been inserted and ligated complementary to said single stranded termini.

2. The method of claim 1, wherein the selected tab site is a pre-existing restriction enzyme site.

3. The method of claim 2, wherein the pre-existing restriction enzyme site, when cleaved, has a four base-5' overhang.

4. The method of claim 2, wherein the pre-existing restriction enzyme site, when cleaved, has a two base-5' overhang.

5. The method of claim 2, wherein the pre-existing restriction enzyme site, when cleaved, has a two base-3' overhang.

6. The method of claim 2, wherein the pre-existing restriction enzyme site, when cleaved, as a four base-3' overhang.